United States Patent
Dalal et al.

(10) Patent No.: US 9,625,402 B2
(45) Date of Patent: Apr. 18, 2017

(54) METHOD AND APPARATUS FOR DETECTION OF DEFECTIVE BRAKES

(71) Applicant: Xerox Corporation, Norwalk, CT (US)

(72) Inventors: Edul N. Dalal, Webster, NY (US); Wencheng Wu, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 349 days.

(21) Appl. No.: 14/051,225

(22) Filed: Oct. 10, 2013

(65) Prior Publication Data

US 2015/0103160 A1   Apr. 16, 2015

(51) Int. Cl.
G01M 17/02 (2006.01)
G01N 25/72 (2006.01)
G06T 7/20 (2017.01)
G06T 7/00 (2017.01)

(52) U.S. Cl.
CPC .......... *G01N 25/72* (2013.01); *G01M 17/027* (2013.01); *G06T 7/0004* (2013.01); *G06T 7/20* (2013.01); *G06T 2207/10016* (2013.01); *G06T 2207/10048* (2013.01); *G06T 2207/30164* (2013.01)

(58) Field of Classification Search
USPC ........................................................ 348/125
See application file for complete search history.

(56) References Cited

U.S. PATENT DOCUMENTS

| | | | |
|---|---|---|---|
| 2002/0092347 A1* | 7/2002 | Niekerk | B60C 23/009 73/146.2 |
| 2008/0028846 A1* | 2/2008 | Heath | G01M 17/027 73/146 |
| 2011/0022253 A1* | 1/2011 | Chen | B61L 1/14 701/19 |
| 2013/0088600 A1 | 4/2013 | Wu et al. | |
| 2013/0229517 A1 | 9/2013 | Kozitsky et al. | |

OTHER PUBLICATIONS

D. L. Richard, "Using Infrared Technology to Detect Hot or Defective Brakes on Trucks," Report No. CDOT-DTDR-2004-15, Colorado Department of Transportation, Aug. 2004, consists of 72 pages.

* cited by examiner

*Primary Examiner* — Mikhail Itskovich (57) ABSTRACT

A method, non-transitory computer readable medium, and apparatus for detecting defective brakes are disclosed. For example, the method detects that a wheel of a vehicle is in a position to be read by an infrared (IR) thermometer, signals the IR thermometer to take a temperature measurement of a brake of the wheel, receives the temperature measurement of the brake and determines that a defective brake condition exists when the temperature measurement of the brake is outside a temperature range.

11 Claims, 4 Drawing Sheets

METHOD AND APPARATUS FOR DETECTION OF DEFECTIVE BRAKES

The present disclosure relates generally to automated analysis of vehicles for highway safety and, more particularly, to a method and an apparatus for detection of defective brakes to prevent brake failure.

BACKGROUND

High brake temperatures can lead to brake fade, which can cause catastrophic brake failure. Brake failure is a serious traffic hazard, especially in heavy transport vehicles, such as buses, trucks and tractor-trailers. For example, a loss of braking capability on the highways or roadways could lead to serious accidents and fatalities. Consequently, the Department of Transportation in many states perform spot checks of heavy vehicles such as trucks on their highways.

Typically, checking brakes on a highway involves stopping the truck and dismantling and examining the brakes. However, this process is very expensive and time consuming. The labor involved can be costly, as well as the loss of truck and driver time involved in pulling over the trucks, queuing them up, inspecting them and completing the associated paperwork.

SUMMARY

According to aspects illustrated herein, there are provided a method, a non-transitory computer readable medium, and an apparatus for detecting defective brakes. One disclosed feature of the embodiments is a method that detects that a wheel of a vehicle is in a position to be read by an infrared (IR) thermometer, signals the IR thermometer to take a temperature measurement of a brake of the wheel, receives the temperature measurement of the brake and determines that a defective brake condition exists when the temperature measurement of the brake is outside a temperature range.

Another disclosed feature of the embodiments is a non-transitory computer-readable medium having stored thereon a plurality of instructions, the plurality of instructions including instructions which, when executed by a processor, cause the processor to perform operations that detects that a wheel of a vehicle is in a position to be read by an infrared (IR) thermometer, signals the IR thermometer to take a temperature measurement of a brake of the wheel, receives the temperature measurement of the brake and determines that a defective brake condition exists when the temperature measurement of the brake is outside a temperature range.

Another disclosed feature of the embodiments is an apparatus comprising a processor and a computer readable medium storing a plurality of instructions which, when executed by the processor, cause the processor to perform an operation that detects that a wheel of a vehicle is in a position to be read by an infrared (IR) thermometer, signals the IR thermometer to take a temperature measurement of a brake of the wheel, receives the temperature measurement of the brake and determines that a defective brake condition exists when the temperature measurement of the brake is outside a temperature range.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure broadly discloses a method and non-transitory computer-readable medium for detecting defective brakes. As discussed above, high brake temperatures can lead to brake fade, which can cause catastrophic brake failure. Brake failure is a serious traffic hazard, especially in heavy transport vehicles, such as buses, trucks and tractor-trailers. For example, a loss of brakes on the highways or roadways could lead to serious accidents and fatalities. Consequently, the Department of Transportation in many states perform spot checks of trucks on their highways. However, checking brakes can be a time consuming and expensive process.

One embodiment of the present disclosure provides a method and apparatus for detecting defective brakes. In one embodiment, the method may be automated such that defective brake conditions in vehicles may be detected without the need to stop vehicles or dismantling and examining the brakes by mechanics. Thus, the methods disclosed in the present disclosure provide a more efficient and automated process for detecting defective brakes in vehicles to prevent catastrophic brake failure. This leads to significant cost savings and reduced down time for vehicles, such as trucks and tractor-trailers.

Figure 1:
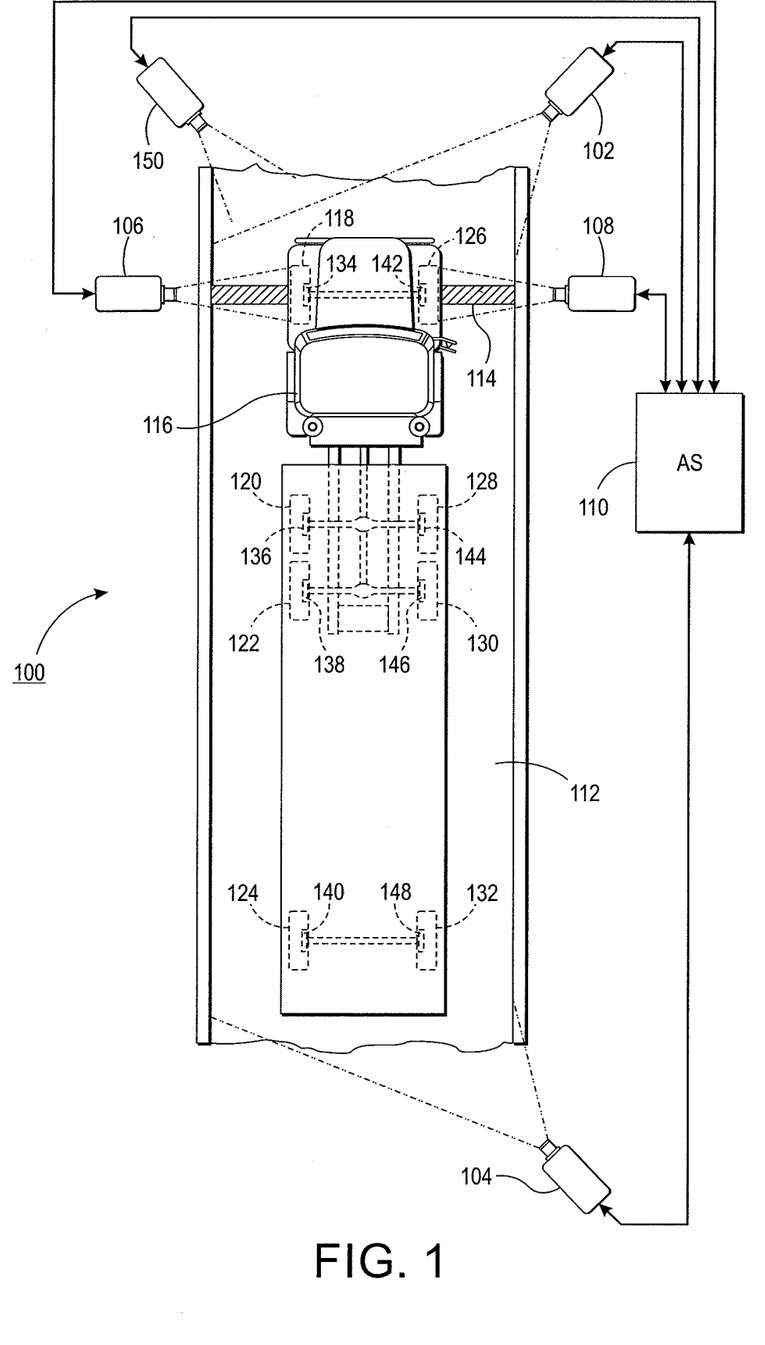
FIG. 1 illustrates an example system for detecting defective brakes in a dedicated lane.

FIG. 1 illustrates an example system 100 for detecting defective brakes in a vehicle in a dedicated lane. In one embodiment, the system 100 may include a dedicated lane 112 and a minimum of two infrared (IR) thermometers 106 and 108 and a video camera 102. In one embodiment, the IR thermometers 106 and 108 may be standard low cost spot measurement IR thermometers. In one embodiment, the video camera 102 may be a standard red green blue (RGB) video camera.

In one embodiment, the IR thermometer 106 may be aimed in a target zone 114 from a left side and the IR thermometer 108 may be aimed in the target zone 114 from a right side. The video camera 102 may be also aimed at the target zone 114 from the front or from the rear to monitor the target zone 114. In one embodiment, the IR thermometers 106 and 108 and the video camera 102 may be in communication with and controlled, via either a wired or wireless connection, by an application server (AS) 110.

In one embodiment, the AS 110 may be a general purpose computer, processor or centralized controller. For example, the AS 110 may be deployed as a general purpose computer illustrated in FIG. 4 and described below. The AS 110 may be located either near the dedicated lane 112 or located remotely from the dedicated lane 112. The AS 110 may receive and analyze the images captured by the video camera 102 and signal the IR thermometers 106 and 108 to take a temperature measurement based upon the analysis of the images of the video camera 102.

For example, a vehicle 116 may be driven in the dedicated lane 112 and approach the target zone 114. In one embodiment, the vehicle 116 may be a semi-truck, tractor trailer, bus or any other large vehicle that typical requires a highway inspection. In one embodiment, the vehicle 116 may include a plurality of wheels 118, 120, 122, 124, 126, 128, 130 and 132 that each has a respective brake 134, 136, 138, 140, 142, 144, 146 and 148.

In one embodiment, the IR thermometers 106 and 108 may be positioned and aimed to take a temperature measurement of the brakes 134, 136, 138, 140, 142, 144, 146 and 148. For example, the IR thermometer 106 may take a temperature measurement of the brakes 134, 136, 138 and 140 on the left side and the IR thermometer 106 may take a temperature measurement of the brakes 142, 144, 146 and 148 on the right side.

In one embodiment, if the video camera 102 has a sufficiently high frame rate (e.g., 1000 frames per second (fps) or greater), the AS 110 may receive the image from the video camera 102 and send a signal to the IR thermometers 106 and 108 to take a temperature measurements of the brakes 134 and 142 the moment the video camera 102 captures an image of the wheels 118 and 126 entering the target zone 114.

However, if the frame rate of the video camera 102 is too low (e.g., a standard 30 or 60 fps), a prediction algorithm may be used. For example, a mark (e.g., a painted line or a spot beam from a mounted laser) or several marks may be used before the target zone 114 in the dedicated lane 112. When the video camera 102 captures an image of the wheels 118 and 126 approaching the mark or marks, the AS 110 may calculate or predict when the wheels 118 and 126 will reach the target zone 114 based on two or more consecutive images and send a signal to the IR thermometers 106 and 108 at that time to take a temperature measurement of the brakes 134 and 142. For example, the marks may be used to determine which consecutive images will be used for the prediction.

In one embodiment, the process may be repeated for every brake on each side of the vehicle 116. For example, the process may be repeated when each of the wheels 120, 122, 124, 128, 130 and 132 approach the target zone 114 at different times to take a temperature measurement of the respective brakes 136, 138, 140, 144, 146 and 148.

In one embodiment, the AS 110 may signal the IR thermometer 106 to take multiple temperature measurements continuously as the wheel 118 moves through the target zone 114. At approximately the same time, the AS 110 may signal the IR thermometer 108 to take multiple temperature measurements continuously as the wheel 126 moves through the target zone 114. As a result, an average of the multiple temperature measurements on each wheel may be calculated to determine the temperature of that wheel. Optionally, an outlier removal step may be performed (e.g., trimming away the upper and/or lower five percentile of the measured values) to remove abnormal data before calculating the average for each wheel.

The temperature measurement or measurements for each brake 134, 136, 138, 140, 142, 144, 146 and 148 may be sent to the AS 110 for processing. The temperatures may be compared against a threshold to determine if a defective brake condition is detected on the vehicle 116. In one embodiment, the threshold may simply be a high temperature threshold and a low temperature threshold to determine if a hot brake condition exists indicating imminent brake failure or a cold brake condition exists indicating that a brake has already failed.

In another embodiment, the temperature threshold may be set as a temperature range, e.g., consisting of an upper-limit and a lower-limit. In one embodiment, the upper limit is a constant value. In another embodiment, the upper limit is a median or average temperature measurement of each one of the brakes 134, 136, 138, 140, 142, 144, 146 and 148 of the vehicle 116 plus an offset value $O_u$. Here $O_u$ may be a weighted combination of a constant and a (trimmed) standard deviation calculated from the temperature measurement of each one of the brakes 134, 136, 138, 140, 142, 144, 146 and 148 of the vehicle 116. The trimmed standard deviation of a set of measurements is determined by first removing a portion of outlier data (e.g. excluding the top and bottom 10 percent of the data) and then calculating the standard deviation of the trimmed data set. Similarly, in one embodiment, the lower limit is a constant value. In another embodiment, the lower limit is a median or average temperature measurement of each one of the brakes 134, 136, 138, 140, 142, 144, 146 and 148 of the vehicle 116 minus an offset value $O_l$. Here $O_l$ may be a weighted combination of a constant and a (trimmed) standard deviation calculated from the temperature measurement of each one of the brakes 134, 136, 138, 140, 142, 144, 146 and 148 of the vehicle 116. One or more of the weights used in calculating $O_u$ and $O_l$ may be zero. In one embodiment, the temperature range may vary for different vehicles due to size of the vehicle, weight of the vehicle, cargo the vehicle is carrying, environment, driving conditions, and the like.

Thus, each temperature measurement of each brake may be compared to the temperature range to determine if a defective brake condition exists. For example, if a temperature measurement is outside of the temperature range, either above or below, the vehicle 116 may have one or more defective brakes. If a given temperature measurement is above the temperature range, the vehicle 116 may have a hot brake condition indicating imminent brake failure, and if the temperature measurement is below the temperature range, the vehicle 116 may have a brake that has already failed.

In one embodiment, the system 100 may include additional video cameras 104 and 150. For example, the additional camera 104 may be advantageous to capture vehicle identification information, such as a license plate number of the vehicle 116 using automatic license plate recognition (ALPR) technology. In addition, the additional video camera 150 may help provide a more accurate indication of when both wheels 118 and 126 reach the target zone 114 rather than extrapolating based upon an image of only one of the wheels using only video camera 102.

The vehicle identification information may part of a notification that the defective brake condition exists that is sent to a transportation authority. The notification may include the license plate number, a description of the vehicle 116, a location where the system 100 is located, and the like. In one embodiment, the transportation authority may be a highway patrol officer or a state's department of transportation personnel. The notification may be sent via an email, a radio transmission, a text message, a push notification via an application, a fax, an automated telephone call, and the like. In an alternate embodiment, if a dedicated lane is used, an electronic sign may be located at the end of the dedicated lane asking the vehicle 116 to pull over due to a defective brake condition that was detected.

In one embodiment, other means may be used to detect the presence of the wheels 118, 120, 122, 124, 126, 128, 130 and 132 in the target zone 114. For example, electromagnetic, pressure or mechanical means may be used. For example, an inductive loop sensor may be used or a pressure sensor running across the dedicated lane 112. In one embodiment, a combination of the video cameras 102, 104 or 150 and the pressure and mechanical means may be deployed to detect the presence of the wheels 118, 120, 122, 124, 126, 128, 130 and 132 in the target zone 114.

In one embodiment, the IR thermometers 106 and 108 may be in a fixed position or a movable position. For example, the IR thermometers 106 and 108 may be mounted on a fixed position with pan/tilt/zoom (PTZ) capability. In another example, the IR thermometers 106 and 108 may be placed on a gimbal system.

As a result, embodiments of the present disclosure 100 provide an automated system 100 that measures brake temperatures on a vehicle 116. Notably, the vehicle 116 does not need to be stopped (unless defective brakes are detected) nor does the brake need to be disassembled for inspection. As a result, a substantial savings in time and costs are achieved. In addition, the system 100 is deployed with low cost equipment as opposed to using expensive thermal imaging video cameras.

Figure 2:
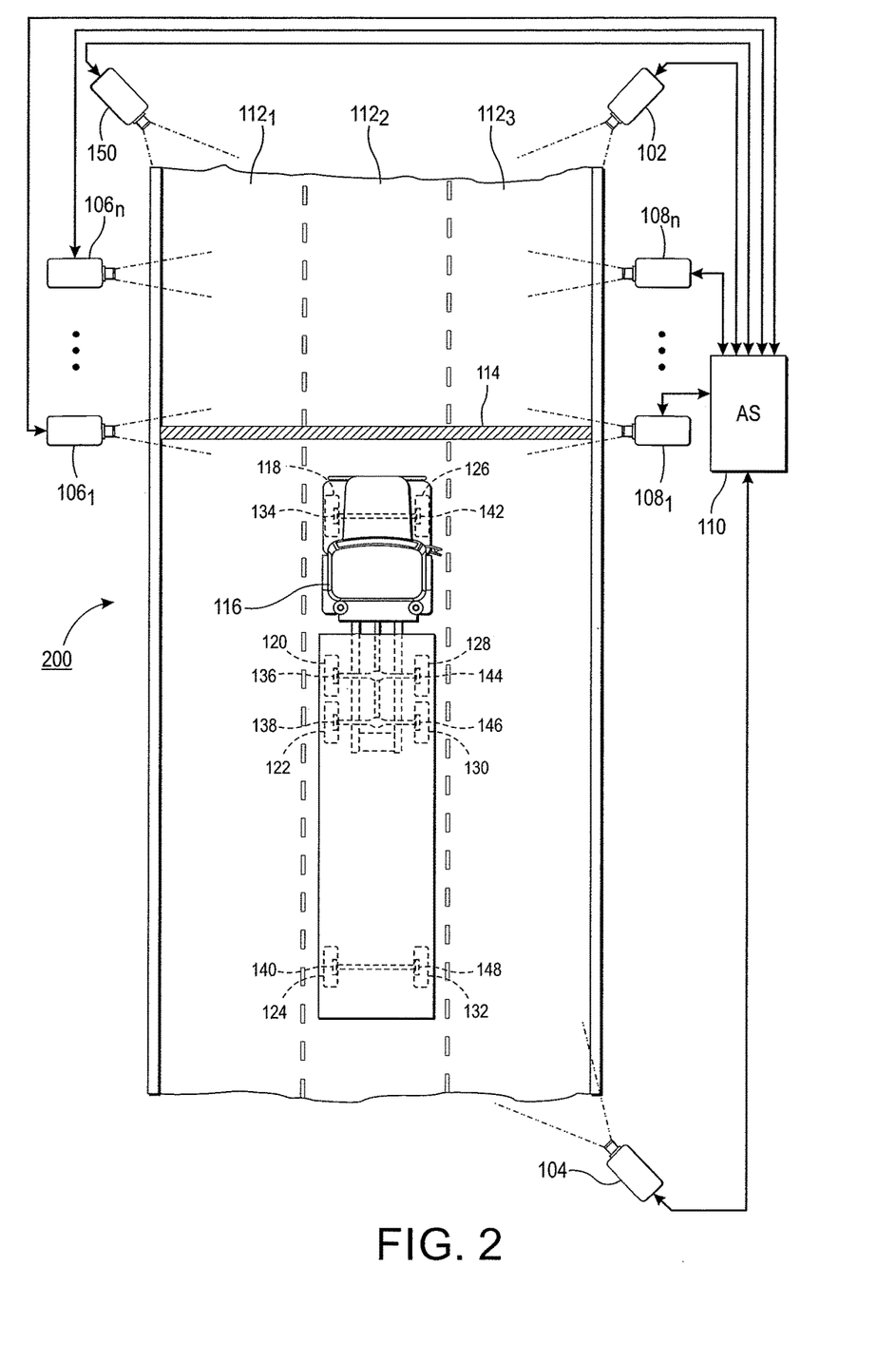
FIG. 2 illustrates an example system for detecting defective brakes without a dedicated lane.

FIG. 2 illustrates a second example of a system 200 for detecting defective brakes without a dedicated lane. For example, the system 200 may be deployed on a street or a highway having multiple lanes $112_1$-$112_n$. In one embodiment, the system 200 may be similar to the system 100 in all respects except that additional IR thermometers $106_1$ to $106_n$ and $108_1$ to $108_n$ may be deployed.

In one embodiment, the additional IR thermometers $106_1$ to $106_n$ and $108_1$ to $108_n$ such that multiple temperature measurements may be taken for each brake 134, 136, 138, 140, 142, 144, 146 and 148 of each respective wheel 118, 120, 122, 124, 126, 128, 130 and 132 as it enters and passes the target zone 114. The multiple temperature measurements may improve the probability that the AS 110 will receive at least one temperature measurement for each one of the brakes 134, 136, 138, 140, 142, 144, 146 and 148 as they are traveling in the lane $112_2$. For example, if no dedicated lane is used, other vehicles may pass between the vehicle 116 and the IR thermometers $106_1$ to $106_n$ and $108_1$ to $108_n$. In other words, other vehicles in lanes $112_1$ and $112_3$ may occlude the measurement of the IR thermometers $106_1$ to $106_n$ and $108_1$ to $108_n$. However, having multiple IR thermometers $106_1$ to $106_n$ and $108_1$ to $108_n$ along a length of a highway may improve the probability that at least one temperature measurement for each of the brakes 134, 136, 138, 140, 142, 144, 146 and 148 will be received.

Furthermore, with the assistance of a video camera or video cameras, appropriate associations between the reading of each IR thermometer $106_1$ to $106_n$ and $108_1$ to $108_n$ and the wheels of each vehicle at each lane can be established (e.g., through license plate recognition (LPR), vehicle tracking, etc.). The distance between multiple IR thermometers $106_1$ to $106_n$ and $108_1$ to $108_n$ can be sufficiently close (so that it can be assumed that all readings are from the same vehicle) or significantly far apart, e.g., up to several miles away. In the latter case, the identification of the vehicle (e.g., through LPR) and the temperature measurements need to be linked and communicated to a central processing unit (e.g., AS 110) to perform the final analysis regarding whether the vehicle has defective brakes.

Figure 3:
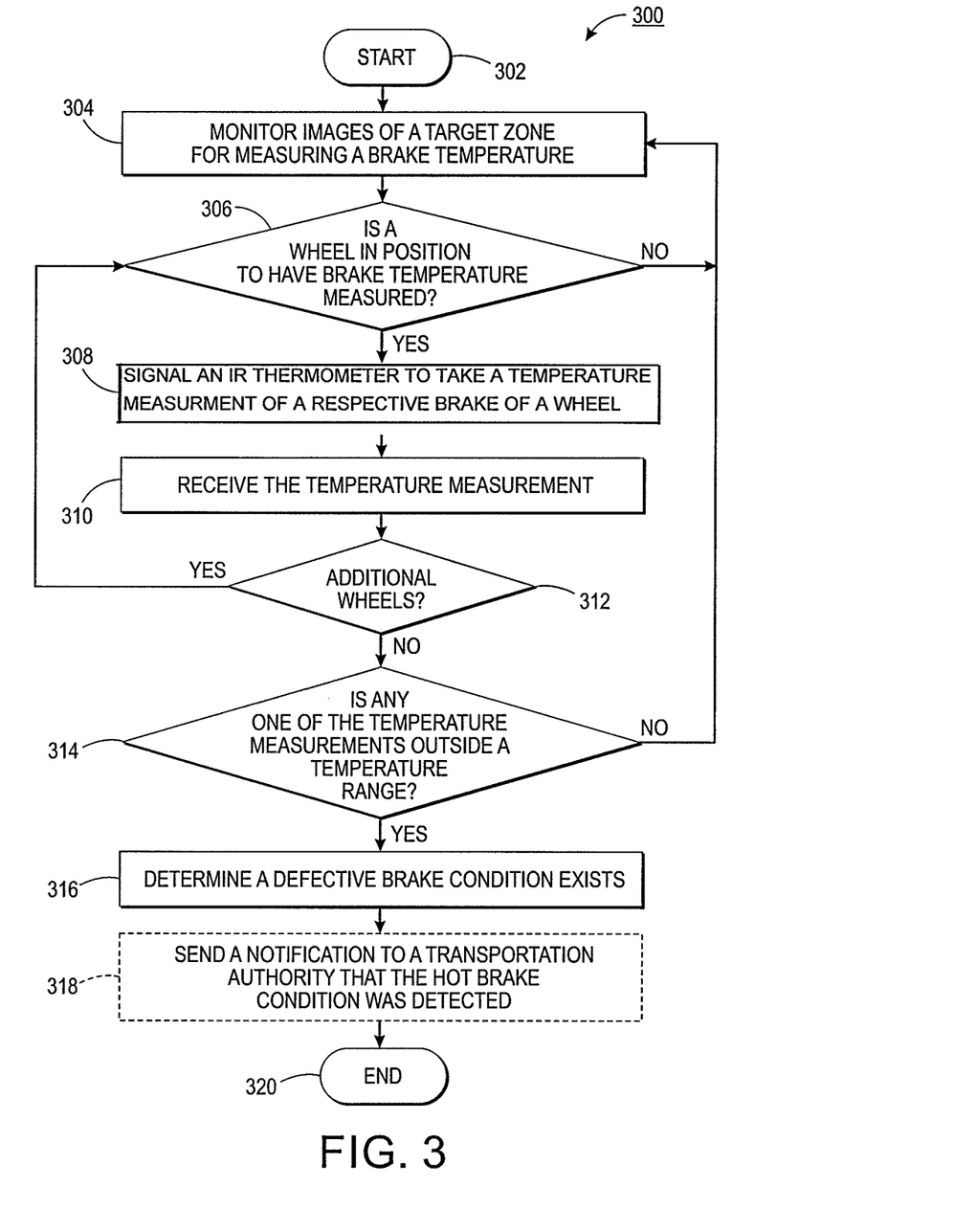
FIG. 3 illustrates an example flowchart of a method for detecting defective brakes.
Figure 4:
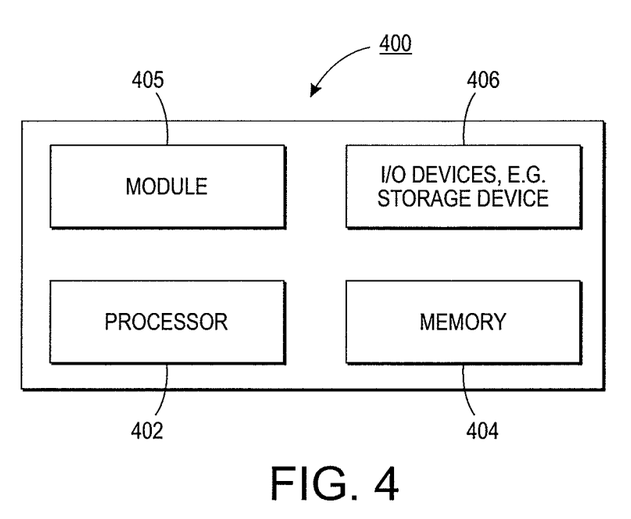
FIG. 4 illustrates a high-level block diagram of a general-purpose computer suitable for use in performing the functions described herein.

FIG. 3 illustrates a flowchart of a method 300 for detecting defective brakes. In one embodiment, one or more steps or operations of the method 300 may be performed by the AS 110 of the system 100 or 200 or a general-purpose computer as illustrated in FIG. 4 and discussed below.

The method 300 begins at step 302. At step 304, the method 300 monitors images of a target zone for measuring a brake temperature. In one embodiment, the target zone may be monitored by one or more video cameras located around the target zone (e.g., to the left and right, front and back, front left, front right and back, and the like). In one embodiment, the video cameras may be standard RGB video cameras.

In another embodiment, the target zone may be monitored by a mechanical or pressure means. For example, an inductive loop sensor or a pressure counter may be placed before the target zone to indicate that a wheel is about to enter the target zone.

At step 306, the method 300 determines if a wheel of a vehicle is in a position to have a brake temperature measured. In one embodiment, the method 300 at step 306 may determine if one or more of the wheels (e.g., a left wheel and/or a right wheel) are in a position to have a brake temperature measured for each wheel. For example, if a video camera is being used and the frame rate is high enough (e.g., greater than 1000 fps), the image captured from the video camera may be used to determine when each wheel is in position. In another embodiment, if the video camera has a slower frame rate, a prediction may be made based upon processing of two or more consecutive images from the video camera. For example, a mark or marks (e.g., a painted line on the ground, a laser line, and the like) may be used to determine which consecutive images will be used for the prediction. In another example, if the inductive loop sensor or the pressure counter is used, the sensor or counter may signal that the wheels are in position when traversed.

If none of the wheels are in position, the method 300 returns to step 304 and the method 300 continues to monitor the images. If a wheel is in position, the method 300 proceeds to step 308. At step 308, the method 300 signals an IR thermometer to take a temperature measurement of a respective brake of a wheel.

In one embodiment, a plurality of IR thermometers may be signaled to take a temperature measurement of a respective wheel. For example, a first IR thermometer may be positioned on a left side to take a temperature measurement of a brake of a wheel on the left side. In addition, a second IR thermometer may be positioned on a right side to take a temperature measurement of a brake of a wheel on the right side. In one embodiment, the first IR thermometer may take a temperature measurement of each brake of all the wheels on the left side. Correspondingly, the second IR thermometer may take a temperature measurement of each brake of all the wheels on the right side.

In one embodiment, the IR thermometers may take continuous temperature measurements as the wheel passes through the target zone and past the left and right IR thermometers. As a result, an average of the multiple temperature measurements may be calculated for each brake of each wheel. Optionally, an outlier removal step may be performed (e.g., trimming away the upper and/or lower five percentile) to remove abnormal data before calculating the average.

In one embodiment, a plurality of IR thermometers may be deployed along a road or highway on both sides. For example, as a vehicle travels down the highway, the vehicle may pass consecutive IR thermometers spaced apart on the left side and the right side. This allows a proper temperature measurement to be taken of each brake of the vehicle if the vehicle is traveling in a non-dedicated lane or a highway with multiple lanes. For example, other cars may occlude the view of the IR thermometer on either side at any moment. Using multiple IR thermometers located over a distance on both sides of the road improves the probability that at least one of the IR thermometers will be able to take a temperature measurement of each brake of the vehicle without being occluded.

At step 310, the method 300 receives the temperature measurement of the brake. For example, the AS may receive a temperature measurement for each brake of a vehicle. In one embodiment, the temperature measurements may include information identifying which brake of the vehicle is associated with each temperature measurement.

At step 312, the method 300 may determine if there any additional wheels remaining on the vehicle that need to have a brake temperature measured. If additional wheels of the vehicle remain, the method may return to step 306 and perform steps 306, 308 and 310 until a brake temperature of each brake of each wheel is measured.

At step 314, the method 300 determines if any one of the temperature measurements is outside a temperature range. For example, the temperatures may be compared against a temperature range, e.g., consisting of an upper-limit and a lower-limit, to determine if a defective brake condition is detected on the vehicle 116. In one embodiment, the upper limit is a constant value. In another embodiment, the upper limit is a median or average temperature measurement of each one of the brakes of the vehicle plus an offset value $O_u$. Here $O_u$ may be a weighted combination of a constant and a (trimmed) standard deviation calculated from the temperature measurement of each of the brakes of the vehicle. The trimmed standard deviation of a set of measurements is determined by first removing a portion of outlier data (e.g. excluding the top and bottom 10 percent of the data) and then calculating the standard deviation of the trimmed data set. Similarly, in one embodiment, the lower limit is a constant value. In another embodiment, the lower limit is a median or average temperature measurement of each of the brakes of the vehicle minus an offset value $O_l$. Here $O_l$ may be a weighted combination of a constant and a (trimmed) standard deviation calculated from the temperature measurement of each of the brakes of the vehicle. One or more of the weights used in calculating $O_u$ and $O_l$ may be zero. In one embodiment, the temperature range may vary for different vehicles due to size of the vehicle, weight of the vehicle, cargo the vehicle is carrying, environment, driving conditions, and the like.

If any one of the temperature measurements is above the temperature range, the vehicle may be experiencing a hot brake condition that indicates imminent brake failure. If any one of the temperature measurements is below the temperature range, the vehicle may be experiencing a cold brake condition that indicates a brake has already failed.

If none of the temperature measurements are outside the temperature range, the method 300 returns to step 304 to continue monitoring the images. If any one of the temperature measurements is outside the temperature range, the method 300 proceeds to step 316. At step 316, the method 300 determines that a defective brake condition exists.

At optional step 318, the method 300 may send a notification to a transportation authority that the defective brake condition was detected. The notification may include vehicle identification information such as, for example, a license plate number, a description of the vehicle, which highway or road the vehicle is traveling one, and the like. In one embodiment, the vehicle identification information may be obtained using a video camera that is used to perform the monitoring in step 304.

In one embodiment, the transportation authority may be a highway patrol officer or a state's department of transportation personnel. The notification may be sent via an email, radio transmission, text message, push notification via an application, a fax, an automated telephone call, and the like. The method 300 then proceeds to step 320 where the method 300 ends.

It should be noted that although not explicitly specified, one or more steps, functions, or operations of the method 300 described above may include a storing, displaying and/or outputting step as required for a particular application. In other words, any data, records, fields, and/or intermediate results discussed in the methods can be stored, displayed, and/or outputted to another device as required for a particular application. Furthermore, steps, functions, or operations in FIG. 3 that recite a determining operation, or involve a decision, do not necessarily require that both branches of the determining operation be practiced. In other words, one of the branches of the determining operation can be deemed as an optional step.

FIG. 4 depicts a high-level block diagram of a general-purpose computer suitable for use in performing the functions described herein. As depicted in FIG. 4, the system 400 comprises a processor element 402 (e.g., a CPU), a memory 404, e.g., random access memory (RAM) and/or read only memory (ROM), a module 405 for detecting defective brakes, and various input/output devices 406 (e.g., storage devices, including but not limited to, a tape drive, a floppy drive, a hard disk drive or a compact disk drive, a receiver, a transmitter, a speaker, a display, a speech synthesizer, an output device (such as a graphic display, printer, and the like), an output port, and a user input device (such as a keyboard, a keypad, a mouse, and the like)).

It should be noted that the present disclosure can be implemented in software and/or in a combination of software and hardware, e.g., using application specific integrated circuits (ASIC), a general purpose computer or any other hardware equivalents, e.g., computer readable instructions pertaining to the method(s) discussed above can be used to configure a hardware processor to perform the steps of the above disclosed methods. In one embodiment, the present module or process 405 for detecting defective brakes can be loaded into memory 404 and executed by processor 402 to implement the functions as discussed above. As such, the present method 405 for detecting defective brakes (including associated data structures) of the present disclosure can be stored on a non-transitory (e.g., physical and tangible) computer readable storage medium, e.g., RAM memory, magnetic or optical drive or diskette and the like. For example, the hardware processor 402 can be programmed or configured with instructions (e.g., computer readable instructions) to perform the steps, functions, or operations of method 300.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for detecting a defective brake condition, the method comprising:

detecting, by a processor of an application server that is in communication with an infrared (IR) thermometer and a video camera, that a wheel of a vehicle is in a position to be read by the IR thermometer that measures a spot temperature based upon an image captured by the video camera, wherein the detecting comprises:

signaling, by the processor, the video camera to capture a plurality of consecutive images of the wheel at a mark that is located before a target zone that includes the IR thermometer;

receiving, by the processor, the plurality of consecutive images; and analyzing, by the processor, two or more consecutive images of the plurality consecutive images to calculate a predicted time of when the wheel will reach the target zone based upon an image processing of the two or more consecutive images captured by the video camera, wherein the two or more consecutive images are selected based on images of the wheel that are approaching the mark;

signaling, by the processor, the IR thermometer to take a plurality of temperature measurements of the wheel at the predicted time in response to the detecting via the video camera;

receiving, by the processor, the plurality temperature measurements of the wheel;

determining, by the processor, a brake temperature based on the plurality of temperature measurements of the wheel; and determining, by the processor, that the defective brake condition exists when the brake temperature is outside a temperature range.

2. The method of claim 1, wherein the IR thermometer takes continuous temperature measurements of the wheel as the wheel passes the IR thermometer.

3. The method of claim 1, wherein the temperature range comprises an upper limit and a lower limit, wherein calculating the upper limit comprises:

averaging, via the processor, the plurality of temperature measurements of each one of a plurality of wheels of the vehicle; and adding, via the processor, a positive offset value, wherein calculating the lower limit comprises averaging, via the processor, the plurality of temperature measurements of the each one of the plurality of wheels of the vehicle; and subtracting, via the processor, a negative offset value.

4. The method of claim 1, wherein the signaling comprises signaling a plurality of IR thermometers to take the plurality of temperature measurements as the wheel is moving.

5. The method of claim 1, further comprising:

receiving, by the processor, an image of a license plate of the vehicle; and sending, by the processor, a notification comprising a description of the vehicle and the license plate to a transportation authority that the defective brake condition was detected on the vehicle.

6. A non-transitory computer-readable medium storing a plurality of instructions which, when executed by a processor of an application server that is in communication with an infrared (IR) thermometer and a video camera, cause the processor to perform operations for detecting a defective brake condition, the operations comprising:

detecting that a wheel of a vehicle is in a position to be read by the IR thermometer that measures a spot temperature based upon an image captured by the video camera, wherein the detecting comprises:

signaling the video camera to capture a plurality of consecutive images of the wheel at a mark that is located before a target zone that includes the IR thermometer;

receiving the plurality of consecutive images; and analyzing two or more consecutive images of the plurality consecutive images to calculate a predicted time of when the wheel will reach the target zone based upon an image processing of the two or more consecutive images captured by the video camera, wherein the two or more consecutive images are selected based on images of the wheel that are approaching the mark;

signaling the IR thermometer to take a plurality of temperature measurements of the wheel at the predicted time in response to the detecting via the video camera;

receiving the plurality temperature measurements of the wheel;

determining a brake temperature based on the plurality of temperature measurements of the wheel; and determining that the defective brake condition exists when the brake temperature is outside a temperature range.

7. The non-transitory computer-readable medium of claim 6, wherein the IR thermometer takes continuous temperature measurements of the wheel as the wheel passes the IR thermometer.

8. The non-transitory computer-readable medium of claim 6, comprises an upper limit and a lower limit, wherein calculating the upper limit comprises:

averaging the plurality of temperature measurements of each one of a plurality of wheels of the vehicle; and adding a positive offset value, wherein calculating the lower limit comprises averaging the plurality of temperature measurements of the each one of the plurality of wheels of the vehicle; and subtracting a negative offset value.

9. The non-transitory computer-readable medium of claim 6, wherein the signaling comprises signaling a plurality of IR thermometers to take the plurality of temperature measurements as the wheel is moving.

10. The non-transitory computer-readable medium of claim 6, the operations further comprising:

receiving an image of a license plate of the vehicle; and sending a notification comprising a description of the vehicle and the license plate to a transportation authority that the defective brake condition was detected on the vehicle.

11. A method for detecting a defective brake condition, the method comprising:

monitoring, by a processor of an application server that is in communication with a plurality of infrared (IR) thermometers and a video camera, a mark located before a target zone to detect when one or more wheels of a vehicle approach the mark via the video camera;

signaling, by the processor, the video camera to capture a plurality of consecutive images of the one or more wheels;

receiving, by the processor, the plurality of consecutive images;

analyzing, by the processor, two or more consecutive images of the plurality consecutive images to calculate a predicted time of when the one or more wheels will reach the target zone based upon an image processing of the two or more consecutive images captured by the video camera, wherein the two or more consecutive images are selected based on images of the one or more wheels that are approaching the mark;

detecting, by the processor, based upon the predicted time that a left wheel of the one or more wheels of the vehicle and a right wheel of the one or more wheels are in a position to be read by a respective one of a plurality infrared (IR) thermometers that each measure a spot temperature;

signaling, by the processor, a first one of the plurality of IR thermometers located on a left side to take a plurality of temperature measurements of a left wheel as the left wheel passes through the target zone;

signaling, by the processor, a second one of the plurality of IR thermometers located on a right side to take a plurality of temperature measurements of a right wheel as the right wheel passes through the target zone;

repeating, by the processor, the detecting, the signaling of the first one of the plurality of IR thermometers and the signaling of the second one of the plurality of IR thermometers for each right wheel and each left wheel of the vehicle;

receiving, by the processor, the plurality of temperature measurements of the each left wheel and the plurality of temperature measurements of the each right wheel of the vehicle;

determining, by the processor, a brake temperature for the each left wheel and the each right wheel based on the plurality of temperature measurements of the each left wheel and the plurality of temperature measurements of the each right wheel, respectively; and determining, by the processor, that the defective brake condition exists when the brake temperature of any one of the each left brake or the each right brake is outside an acceptable temperature range.

* * * * *